United States Patent [19]

Totakura et al.

[11] Patent Number: 5,607,686
[45] Date of Patent: Mar. 4, 1997

[54] POLYMERIC COMPOSITION

[75] Inventors: Nagabhushanam Totakura, North Haven, Conn.; Shalaby W. Shalaby, Anderson, S.C.

[73] Assignee: United States Surgical Corporation, Norwalk, Conn.

[21] Appl. No.: 343,389

[22] Filed: Nov. 22, 1994

[51] Int. Cl.$^6$ .......................... A61L 25/00; A61K 47/36; A61K 47/34
[52] U.S. Cl. .................. 424/426; 514/772.3; 514/772.7; 424/422; 424/435; 523/118
[58] Field of Search .......................... 424/426; 514/772.3

[56] References Cited

U.S. PATENT DOCUMENTS

| | | | |
|---|---|---|---|
| 2,895,950 | 7/1959 | Krieble | 260/89.5 |
| 3,608,070 | 8/1971 | Nouvel | 424/80 |
| 3,700,643 | 10/1972 | Smith et al. | 260/775 AN |
| 3,760,034 | 9/1973 | Critchfield et al. | 260/874 |
| 3,763,071 | 6/1975 | Katzer | 260/29.68 |
| 3,887,699 | 4/1976 | Yolles | 424/19 |
| 3,949,073 | 11/1976 | Daniels et al. | 424/177 |
| 3,992,518 | 12/1976 | Chien et al. | 424/22 |
| 3,997,660 | 12/1976 | Kopecek et al. | 424/78 |
| 4,141,973 | 2/1979 | Balazs | 424/180 |
| 4,238,381 | 12/1980 | Komai et al. | 260/31.2 R |
| 4,267,295 | 5/1981 | Gallop et al. | 526/264 |
| 4,368,320 | 1/1983 | Aldinger et al. | 528/355 |
| 4,450,809 | 5/1984 | Yokoshima et al. | 560/185 |
| 4,532,134 | 7/1985 | Malette et al. | 514/55 |
| 4,543,358 | 9/1985 | Quinlan | 514/368 |
| 4,563,184 | 1/1986 | Korol | 604/368 |
| 4,565,361 | 2/1986 | Kronenthal et al. | 424/22 |
| 4,570,629 | 2/1986 | Widra | 128/156 |
| 4,582,052 | 4/1986 | Dunn et al. | 128/130 |
| 4,631,188 | 12/1986 | Stoy et al. | 424/81 |
| 4,632,975 | 12/1986 | Connell | 528/354 |
| 4,643,734 | 2/1987 | Lin | 623/16 |
| 4,650,665 | 3/1987 | Kronenthal et al. | 424/435 |
| 4,655,777 | 4/1987 | Dunn et al. | 623/16 |
| 4,667,139 | 5/1987 | Hirai et al. | 318/687 |
| 4,683,287 | 7/1987 | Koleske et al. | 528/357 |
| 4,701,320 | 10/1987 | Hasegawa et al. | 424/54 |
| 4,702,917 | 10/1987 | Schindler | 424/422 |
| 4,713,446 | 12/1987 | DeVore et al. | 530/356 |
| 4,722,948 | 2/1988 | Sanderson | 523/115 |
| 4,725,271 | 2/1988 | Korol | 604/368 |
| 4,745,160 | 5/1988 | Churchill et al. | 525/415 |
| 4,767,628 | 8/1988 | Hutchinson | 424/426 |
| 4,780,320 | 10/1988 | Baker | 424/493 |
| 4,841,968 | 6/1989 | Dunn et al. | 128/335.5 |
| 4,875,479 | 10/1989 | Belykh et al. | 128/335.5 |
| 4,882,168 | 11/1989 | Casey et al. | 424/468 |
| 4,883,534 | 11/1989 | Sandham et al. | 106/35 |
| 4,911,926 | 3/1990 | Henry et al. | 424/426 |
| 4,913,897 | 4/1990 | Chrapil et al. | 424/59 |
| 4,938,763 | 7/1990 | Dunn et al. | 604/891.1 |
| 4,950,735 | 8/1990 | Vanderbilt et al. | 528/354 |
| 4,975,271 | 12/1990 | Dunn et al. | 424/49 |
| 4,981,693 | 1/1991 | Higashi et al. | 424/435 |
| 4,981,696 | 1/1991 | Loomis et al. | 424/486 |
| 4,983,689 | 1/1991 | Yu | 525/412 |
| 4,994,277 | 2/1991 | Higham et al. | 424/443 |
| 5,007,940 | 4/1991 | Berg | 623/66 |
| 5,013,553 | 5/1991 | Southard | 424/426 |
| 5,019,094 | 5/1991 | Bezwada et al. | 606/230 |
| 5,059,123 | 10/1991 | Jernberg | 433/215 |
| 5,068,107 | 11/1991 | Hollibush et al. | 424/435 |
| 5,068,220 | 11/1991 | Vanderbilt et al. | 514/3 |
| 5,077,049 | 12/1991 | Dunn et al. | 424/426 |

(List continued on next page.)

FOREIGN PATENT DOCUMENTS

| | | |
|---|---|---|
| 0126827 | 11/1983 | European Pat. Off. . |
| 0261470 | 9/1987 | European Pat. Off. . |
| 539751 | 5/1993 | European Pat. Off. . |
| 562612 | 9/1993 | European Pat. Off. . |
| 610731 | 8/1994 | European Pat. Off. . |
| 59-11315 | 1/1984 | Japan . |
| 9101126 | 2/1981 | WIPO . |
| 8404311 | 11/1984 | WIPO . |
| 90/03768 | 4/1990 | WIPO . |
| 9100720 | 1/1991 | WIPO . |
| 91/01126 | 2/1991 | WIPO . |
| 9200718 | 1/1992 | WIPO . |

OTHER PUBLICATIONS

Muth et al., *Chemical Abstracts*, vol. 119, (1993), #256581.
Reexam File History–901803037 PA Newswire "Atrix Starts Phase III Trials for the Perio Product Containing Doxycycline"–Jan 23, 1995.

*Primary Examiner*—Carlos Azpuru

[57] ABSTRACT

A polymeric composition for use in medicine includes a hydrophobic bioabsorbable polymer admixed with a hydrophilic liquid polymer wherein the polymeric composition undergoes macroscopic phase separation on contact with aqueous media. The polymeric composition optionally includes a medicinal agent. The polymeric composition may be deposited as a permeable, semipermeable or occlusive irregular mass, regular mass, film or foam over a suitable surface such viable body tissue. Bioabsorbable implants formed from the polymeric composition may assume a variety of three dimensional configurations such as planar, spherical, cylindrical, rectangular and polygonal.

21 Claims, No Drawings

U.S. PATENT DOCUMENTS

| | | | |
|---|---|---|---|
| 5,080,893 | 1/1992 | Goldberg et al. | 514/57 |
| 5,085,866 | 2/1992 | Cowsar et al. | 424/481 |
| 5,093,319 | 3/1992 | Higham et al. | 514/55 |
| 5,094,841 | 3/1992 | Fine | 424/52 |
| 5,124,073 | 6/1992 | Goffnig et al. | 252/314 |
| 5,126,141 | 6/1992 | Henry | 424/423 |
| 5,133,981 | 7/1992 | Hankrader et al. | 424/195.1 |
| 5,135,751 | 8/1992 | Henry et al. | 424/426 |
| 5,143,730 | 9/1992 | Fues et al. | 424/426 |
| 5,160,737 | 11/1992 | Friedman et al. | 424/401 |
| 5,175,000 | 12/1992 | Godowski et al. | 424/426 |
| 5,192,536 | 3/1993 | Huprich | 424/78.08 |
| 5,197,882 | 3/1993 | Jernberg | 424/426 |
| 5,230,895 | 7/1993 | Czarnecki et al. | 424/422 |
| 5,250,584 | 10/1993 | Ikada et al. | 523/114 |
| 5,264,214 | 11/1993 | Rhee et al. | 424/422 |
| 5,268,178 | 12/1993 | Calhoun et al. | 424/426 |
| 5,270,300 | 12/1993 | Hunziker | 514/12 |
| 5,278,201 | 1/1994 | Dunn et al. | 523/113 |
| 5,278,202 | 1/1994 | Dunn et al. | 523/113 |
| 5,286,178 | 2/1994 | Schaef | 424/426 |
| 5,286,763 | 2/1994 | Gerhart et al. | 514/772.4 |
| 5,308,623 | 5/1994 | Flies et al. | 424/426 |
| 5,318,780 | 6/1994 | Viegas et al. | |
| 5,322,925 | 6/1994 | Muth et al. | 606/230 |
| 5,324,519 | 6/1994 | Dunn et al. | 424/426 |
| 5,324,520 | 6/1994 | Dunn et al. | 424/435 |
| 5,330,763 | 7/1994 | Gole et al. | 424/484 |
| 5,330,764 | 7/1994 | Gole et al. | 424/484 |
| 5,340,849 | 8/1994 | Dunn et al. | 523/113 |
| 5,350,573 | 9/1994 | Goldberg et al. | 424/78.06 |
| 5,368,859 | 11/1994 | Dunn et al. | 424/426 |

POLYMERIC COMPOSITION

BACKGROUND

1. Technical Field

The present disclosure relates to polymeric compositions used in medicine and, more particularly, to liquid polymer mixtures which are capable of undergoing macrophase separation in aqueous environments to form bioabsorbable implants.

2. Background of Related Art

Bioabsorbable polymers are well-known for use in medicine. Typical formulations of such polymers are used in wound closure and wound repair, e.g., absorbable sutures, absorbable staples, absorbable osteosynthesis screws, absorbable hernia repair mesh and the like. Bioabsorbable polymers are also used for degradable drug delivery devices. The above items are ordinarily manufactured, e.g., by molding, drawing or spinning into the preformed final product which is then used as indicated by a surgeon.

In certain circumstances customized implant forms and shapes are necessary that are not provided by preformed shapes. Wound dressings or adhesion barriers of unique shape are frequently applied to irregularly shaped surfaces. The surgeon may need to cut the adhesion barrier or wound dressing to provide the appropriate shape. Unfortunately, such manipulations by the surgeon may be time consuming and, despite care and skill, the dressing or barrier may not adequately conform and/or adhere to the underlying tissue terrain.

Small voids or cavities, e.g., a periodontal pocket, present unique problems relating to treatment of infection or trauma. Ideally, treatment of the periodontium involves preventing or eradicating infection by cleaning and/or antimicrobial therapy and, in certain cases, barrier formation to aid restoration of normal healthy periodontium tissue. Antimicrobial therapy usually involves systemic and/or local administration of antimicrobial drugs. Systemic administration is associated with certain disadvantages, e.g., the time needed to reach effective blood levels at the target site and potential fungal superinfection during antibiotic therapy. Moreover, patient compliance in adhering to an oral dosage regimen is often problematic. Maintaining effective drug levels in a periodontal pocket is difficult in connection with local administration of drugs since dosage forms that do not provide sustained or controlled release are quickly washed away by aqueous secretions in the mouth. Periodontal pockets are often difficult to access without large-scale mutilation of surrounding periodontium. Preformed sustained or controlled release drug delivery systems applied within the mouth, but outside a damaged periodontal pocket may fail to provide effective spatial placement of the drug due to crevicular plasma flow preventing contact of the drug with the target locus. Ideally, therapy should be directed to spatial placement and sustained and/or controlled temporal delivery directly within the affected periodontal pocket. An irregularly shaped periodontal pocket that is difficult to access is not easily amendable to receiving a preformed drug delivery device, i.e., the device would be difficult to insert and not adequately provide proper or complete spatial placement over terrain within the cavity.

Natural repair or restoration of the periodontium involves migration and replacement of ligament cells, epithelial cells and fibroblasts in the injured area. Ligament cells provide a strong bond for teeth and other hard tissue structures. The presence of a predominant amount of cells which are not soft connective tissue cells, e.g., epithelial cells, at an injury repair site creates a soft or weak bond to surrounding hard tissue. A barrier to epithelial cells and fibroblasts allows a predominance of ligament cells to populate the injured area and creation of a strong bond to surrounding hard tissues. As with drug delivery devices, a preformed barrier would not fit easily into and conform to the complex geometry of a target location to provide an effective barrier to epithelial cells and fibroblast migration.

As a consequence, attempts have been made to formulate surgical aids that provide in-situ forming drug delivery devices, barriers and dressings. U.S Pat. No. 4,911,926 describes aqueous and non-aqueous compositions made of polyoxyalkylene block copolymers which form gels at mammalian body temperatures for use in reducing post-operative adhesion formation following surgery to the peritoneal or pleural cavities. Other gel forming compositions have been developed for preventing adhesions, e.g., U.S. Pat. Nos. 5,093,319 (chitin derivative soluble in aqueous solutions containing dilute acids), 5,080,893 (aqueous solutions of hydrophilic polymeric materials of high molecular weight), 4,994,277 (xanthan gum), 4,532,134 (chitosan coagulum), and 4,141,973 (hyaluronic acid).

Another approach to making implants involves dissolving a polymer in monomeric solvent to provide a desirable form of the polymer. Examples of such monomeric solvents include halogenated alkanes, ketones or aromatic hydrocarbons. The resulting mixture is applied to a desired substrate and a solid film or coating is produced when the solvent evaporates. However, concerns about the fugacity and/or toxicity of such monomeric organic solvents and the danger associated with explosion, or absorption by localized viable tissue has created a distinct need for less harmful substrates.

Certain biodegradable in-situ forming implants and methods of forming them are described in U.S. Patent Nos. 5,278,201, 5,077,049 and 4,938,763. As described therein, a thermoplastic system involves dissolving a solid, linear-chain, water-insoluble biodegradable polymer in a monomeric solvent to form a liquid solution. After the polymer solution is placed into the body, the monomeric solvent dissipates or diffuses away from the polymer, leaving the polymer to coagulate or solidify, leaving a solid structure. A drug may be added to the polymer solution to form a homogeneous solution or be dispersed to form a suspension or dispersion of drug within the polymeric solution. The thermoplastic system may be placed into a syringe and injected into the body. U.S. Pat. No. 5,077,049 describes the thermoplastic system for use in regenerating the periodontium.

U.S. Pat. No. 5,236,355 is directed to an apparatus for the treatment of peridontal disease. As described therein, sustained release compositions for the local administration of a therapeutic are administered as a plurality of dry, discrete microparticles of at least one therapeutic agent dispersed in a matrix made of a biocompatible and biodegradable polymer. The microencapsulated compositions may be produced by a phase separation process which employs silicone fluids as hardening agents. Methylene chloride is used to disolve the biodegradable polymer prior to mixing with the silicone.

Unfortunately, the use of monomeric solvents as described above leads to irritation of surrounding tissue and nerve endings since monomeric solvents are absorbed quickly and cause localized hypertonicity and tissue dehydration. The result is pain in the area of implant which can be associated with tissue necrosis. Moreover rapid dissipation of the monomeric solvent leads to shrinkage of the implant and non-uniform changes in its dimensions due to rapid uneven precipitation. Consequently, there is a need for in-situ forming implants that overcome the above described drawbacks. Such in-situ forming implants would present a distinct advantage over preformed implants and the above mentioned irritating in-situ forming implants.

SUMMARY

A polymeric composition is disclosed which includes a hydrophobic bioabsorbable polymer admixed with a hydrophilic liquid polymer such that the polymeric composition undergoes macroscopic phase separation on contact with an aqueous environment. The hydrophobic bioabsorbable polymer may be one or more polyhydroxyacids, polylactones, polycarbonates, polyetheresters, polyanhydrides, polyesteramides, polyorthoesters, polysaccharides, poly(alkylene oxide) containing polymers, and copolymers, terpolymers or blends thereof. Suitable hydrophilic liquid polymers include one or more poly(alkylene oxide) ethers, poly(alkylene oxides) and oxalates of polyoxyalkylene oxides. The polymeric composition optionally includes a suitable medicinal agent.

A method of forming a bioabsorbable implant is disclosed which includes providing a hydrophobic bioabsorbable polymer, providing a hydrophilic liquid polymer and mixing the hydrophobic bioabsorbable polymer with the hydrophilic liquid polymer to form a liquid mixture. The mixture is contacted with an aqueous liquid which causes macroscopic phase separation of the hydrophobic polymer and the bioabsorbable implant is deposited on a suitable surface and/or within the volume of a target site. The implant may be deposited in the form of an irregular mass, a regular mass, film or foam. The mixture may optionally include a suitable medicinal agent. In one aspect, the mixture is contacted with aqueous media by spraying, injecting or pouring the mixture onto or into the aqueous media. Suitable surfaces for depositing the implant include all surfaces on or in a living creature associated with aqueous secretion such as mouth surfaces including the periodontium, organ surfaces, wound surfaces and/or the suture line of a wound.

DESCRIPTION OF PREFERRED EMBODIMENTS

The polymeric composition undergoes phase separation and forms bioabsorbable implants when contacted with aqueous media. It is especially useful for focal drug delivery, protecting wound sites and/or preventing adhesions.

In a preferred embodiment, the polymeric composition undergoes in-situ phase separation and provides an implant with maximum adaptation and conformance to the configuration manifest by the complex geometry of a biological target site. The resulting implant is biomechanically compatible with adjacent tissue and induces little or no physiochemical or mechanical trauma during or following its formation.

The polymeric composition includes a hydrophobic bioabsorbable polymer and a hydrophilic liquid polymer that are fully miscible or partially miscible with each other. Such fully miscible polymeric compositions form isotropic solutions while such partially miscible polymer compositions produce dispersions such as emulsions or suspensions. Upon contact with aqueous media, the polymeric composition is destabilized thermodynamically and discrete macrophase separation occurs. Phase separation causes the bioabsorbable polymer to precipitate and form an amorphous, liquid-crystalline or partially crystalline mass. The precipitate may be in the form of an occlusive, permeable or semipermeable irregular mass, regular mass, film or foam, having variable levels of porosity depending on conditions described below.

"Hydrophobic bioabsorbable polymer" as used herein refers to bioabsorbable polymers that are not ordinarily soluble in water, but will either dissolve or otherwise become dispersed, suspended or emulsified in the hydrophilic liquid polymer described below. The degree of hydrophobicity is such that the bioabsorbable polymers will not dissolve in an aqueous environment and be carded away or dissipated along with the hydrophilic liquid polymer. Hydrophobic bioabsorbable polymers used in the polymeric composition are well known and include polyhydroxyacids, polylactones, polycarbonates, polyanhydrides, polyesteramides, polyetheresters, polyorthoesters, polysaccharides, poly(alkylene oxide) containing polymers, and copolymers, terpolymers and blends thereof. Preferred hydrophobic bioabsorbable polymers for use in the polymeric composition are relatively amorphous or semicrystalline and have low glass transition temperatures. Specific examples of hydrophobic bioabsorbable polymers include polyglycolic acid, polylactic acid, polyhydroxybutyric acid, polyhydroxyvaleric acid, polycaprolactone, polytrimethylene carbonate, polydimethyl trimethylene carbonate and copolymers, terpolymers and blends thereof.

In one embodiment, a preferred hydrophobic bioabsorbable polymer is made of a copolymer containing glycolide, lactide and trimethylene carbonate. In a preferred aspect, the polymer includes a block present in an amount of from about 20% to about 80% by weight, which contains about 5% to about 45% by weight glycolide and about 55% to about 95% by weight trimethylene carbonate, and another block present in an amount of from about 20% to about 80% by weight, which contains about 5% to about 45% by weight glycolide and about 55% to about 95% by weight lactide. An example of such a bioabsorbable polymer is a copolymer having about 50% by weight of a block containing about 20% by weight glycolide and about 80% by weight trim ethylene carbonate and about 50% by weight of a block containing about 20% by weight glycolide and about 80% by weight lactide.

In another embodiment, a preferred bioabsorbable polymer is made of a copolymer containing a block of about 20% to about 50% by weight polypropylene oxide and about 50% to about 80% by weight of another block containing about 5% to about 30% glycolide and about 70% to about 95% by weight lactide. An example of such a polymer is a copolymer having about 35% by weight of a block containing polypropylene oxide and about 65% by weight of a block containing about 18% by weight glycolide and about 82% by weight lactide. It should be understood that the above-described particular embodiments, aspects and examples are merely illustrative of preferred hydrophobic bioabsorbable polymers herein and that other combinations of the above-listed polymers are suitable as well.

The above-described hydrophobic bioabsorbable polymer is combined or admixed with a hydrophilic liquid polymer to form mixtures that make up the polymeric composition. "Hydrophilic" liquid polymer, as used herein means liquid polymers that are water miscible, but capable of dissolving or dispersing by suspending or emulsifying the above-described hydrophobic bioabsorbable polymers without acting as a co-solvent that would cause the hydrophobic bioabsorbable polymers to dissolve in aqueous media. The molecules of the hydrophobic bioabsorbable polymers and the hydrophilic liquid polymers are sufficiently interactive to form one phase liquids or, alternatively, to form polyphasic systems such as dispersions which include suspensions or emulsions. Hydrophilic liquid polymers used in making the polymeric compositions include water miscible liquid polyesters and polyethers such as poly(alkyene oxides), oxalates of polyalkylene oxides, polysaccharides, and poly(alkylene oxide) ethers. Preferred hydrophilic liquid polymers include poly(ethylene oxide) methyl ether, polyethylene oxide, block copolymers of alkylene oxides such as polyethylene oxide and polypropylene oxide, polyoxyethylene oxalate and copolymers, terpolymers and blends thereof. In one preferred aspect, polyethylene oxide having a molecular weight of less than 1000 daltons is utilized. In another preferred aspect, copolymers of polyethylene oxide and polypropylene oxide are utilized. Such copolymers are commercially available and sold under the tradename Pluronics®.

The hydrophobic bioabsorbable polymers and hydrophilic liquid polymers are admixed according to conventional techniques known to those with ordinary skill in the art. Stable isotropic solutions containing two or more fully miscible members of the above hydrophobic and hydrophilic polymers are formed as homogeneous mixtures. The polymers are mixed at optionally elevated temperatures and then clarified by techniques which are standard in the art. Examples of the above polymers which form isotropic solutions are mixtures of liquid polyethylene oxide and copolymers based on trimethylene carbonate, glycolide, and lactide. Dispersions such as emulsions and suspensions consist of a dispersed phase distributed throughout a continuous phase. Suspensions herein are dispersions of solid particular hydrophobic bioabsorbable polymer dispersed in a liquid continuous phase of the hydrophilic liquid polymer. Emulsions herein are dispersions of liquified droplets of hydrophobic bioabsorbable polymer dispersed in a liquid continuous phase of the hydrophilic liquid polymer. To achieve the proper degree of dispersion it is necessary to ensure that adequate mixing is achieved. Homogenizers and the like may be used for this purpose.

Adjuvants may be added to stabilize or preserve the solutions and dispersions described above. Such adjuvants include nonionic surfactants which include alcohol ethoxylates, glycerol esters, polyoxethylene esters, and glycol esters of fatty acids. Preferable nonionic surfactants are glycerol esters of stearic, oleic, and/or lauric acid as well as ethylene and/or diethylene glycol esters of fatty acids.

The polymeric composition optionally includes one or more medicinal agents. As used herein, medicinal agent is used in its broadest sense and incudes any substance or mixture of substances that have clinical use. Consequently medicinal agents may or may not have pharmacological activity per se, e.g., a dye. Examples of classes of medicinal agents which may be combined or mixed into the polymeric composition include antimicrobials, analgesics, antipyretics, anesthetics, antiepileptics, antihistamines, anti-inflammatories, cardiovascular drugs, diagnostic agents, sympathomimetics, cholinomimetrics, antimuscarinics, antispasmodics, hormones, growth factors, muscle relaxants, adrenergic neuron blockers, antineoplastics, immunosuppressants, gastrointestinal drugs, diuretics, steroids and enzymes. It is also intended that combinations of medicinal agents can be used.

Polymeric compositions as described herein undergo macroscopic phase separation on contact with aqueous media with eventual diffusion or transport of the hydrophilic phase away from the hydrophobic bioabsorbable polymer phase. Use of hydrophilic liquid polymers minimizes shrinkage of the resulting bioabsorbable deposit and provides a more uniform structure when compared to deposits left from a system incorporating monomeric solvents.

The resulting deposit left by the polymeric compositions may be in the form of an irregular mass, a regular mass, film or foam, each with regular or irregular morphology and/or microporosity depending on the components of the composition, the amount of composition used and the method utilized for applying the composition to a suitable substrate. The ratio of hydrophobic bioabsorbable polymer to hydrophilic liquid polymer in the polymeric composition ranges from about 1:10 wt/wt to about 9:1 wt/wt, with a ratio of 1:1 wt/wt being preferred. A relatively high molecular weight hydrophilic liquid polymer that incorporates a relatively high concentration of hydrophobic bioabsorbable polymer is highly viscous and leaves a foam deposit over or within a substrate on contact with aqueous media. A lower molecular weight hydrophilic liquid polymer having a relatively small concentration of hydrophobic bioabsorbable polymer leaves a thin film or foam over a substrate on contact with aqueous media in, e.g., a tissue space. Permeability of the deposit may also be regulated, e.g., a high concentration of hydrophobic absorbable polymer in a relatively low molecular weight hydrophilic liquid polymer leaves a dense, occlusive deposit on contact with aqueous media. A low concentration of hydrophobic bioabsorbable polymer in a relatively high molecular weight hydrophilic liquid polymer leaves a highly permeable or porous deposit on contact with aqueous media.

Bioabsorbable implants formed by macrophase separation are capable of having a variety of shapes and configurations. The shape may be irregular and amorphous or of a highly ordered external configuration. Examples of regular mass objects include planar films, cylindrical objects, rectangular object and polygonal objects. The shape of the implant is ultimately determined by the surface on which the polymeric composition is deposited and/or the configuration of the cavity that it occupies.

Bioabsorbable implants made from the polymeric composition provide site-specific release of medicinal agents which may be immediate release, delayed release or sustained release. Immediate release systems provide a drug dose instantly. Delayed release systems provide repetitive intermittent dosings of drug. Sustained release systems achieve slow release of a drug over an extended period of time and should maintain a therapeutically effective concentration of drug at the target site. Medicinal agents that are mingled with the hydrophilic liquid polymer are released immediately to the target site. Medicinal agents that are mingled with the bioabsorbable polymer provide delayed or sustained release therapy by diffusion from the interstices contained in the bioabsorbable implant and/or release from the bioabsorbable network as the implant degrades.

A bioabsorbable implant is formed as a deposit when an above-described polymeric composition is contacted with aqueous media. It should be understood that non-aqueous elements may be present in aqueous media. In one aspect, the aqueous media is body fluid associated with various body organs or cavities which can be accessed during surgery. In this manner, a bioabsorbable implant can be formed over or in desirable locations as an adhesion barrier to minimize or prevent formation of post-surgical adhesions. Desirable locations include the peritoneal or pleural cavities, the gastrointestinal tract and any nerve, muscle, tendon, ligament or bone where adhesions may form following surgery or trauma. An adhesion barrier formed by the polymeric composition may be a permeable, semipermeable or occlusive layer of film or foam that can be painted, sprayed, poured or injected on or into the desired locus. In another aspect, a bioabsorbable implant of film or foam can be formed from the polymeric composition and used as a bolster or reinforcement for wound closures involving sutures or other fasteners. In this manner, the wound is closed and the polymeric composition is applied over the wound closure device to protect and reinforce the wound and prevent adhesions. Alternatively, the polymeric composition is applied to the wound, with resulting formation of a film or foam. A wound closure device is then applied through the film or foam such that the film or foam provides a cushion or bolster for the tissue.

Films and foams made in accordance with the disclosure herein adhere to underlying tissue and remain there until the bioabsorbable polymer is degraded and absorbed. The films and foams undergo relatively little shrinkage and thus do not place undo strain on, or pull away from the application site. Moreover, contact of the hydrophilic liquid polymers described herein does not cause dehydration, hypertonicity and pain at the application site when compared to monomeric solvents. It is contemplated that multiple layers of the polymeric composition may be laid over a suitable location.

Films and foams made from the polymeric composition may be applied to external wounds such as cuts, gashes, ulcers and burns to aid healing. Medicinal agents such as wound healing agents and antimicrobials may be incorporated to speed healing of damaged tissues. In this manner, various growth factors, antibiotics and antifungals can be incorporated into the polymeric composition. When the polymeric composition is applied to appropriate locations in the mouth, it can be used as a barrier to prevent epithelial cells from overpopulating areas where connective tissue regeneration is more desirable. Under such circumstances, a growth factor such as epidermal growth factor is contraindicated. The polymeric composition is especially suitable for therapy relating to dental implants and restoration of damage periodontium. Periodontal pockets may be formed by microbial infection or by surgical intervention relating to implanting prosthetic devices such as posts and crowns. Periodontal pockets may be irregularly shaped and difficult to access. Pouring, injecting or spraying the polymeric composition into the periodontal pocket with subsequent macroscopic phase separation provides an implant with maximum adaptation to the configuration and complete geometry of the periodontal pocket. Incorporation of medicinals into the implant provides a drug delivery system which fills the periodontal pocket and further provides a matrix for a suitable medicinal agents such as antimicrobials, soft connective tissue growth enhancers and anti-inflammatory agents.

The following examples are illustrative of specific embodiments of the polymeric compositions and should not be construed as limitations thereof.

EXAMPLE 1

5.0g of a hydrophobic bioabsorbable polymer containing 50% by weight of a first block of 40% by weight glycolide and 60% by weight trimethylene carbonate and 50% by weight of a second block of 20% by weight glycolide and 80% by weight lactide, was placed in 20 ml of polyethylene oxide methyl ether having a molecular weight of 350 daltons. The mixture was heated to 80° C. for 24 hours without stirring. After 24 hours the polymer dissolved completely to form a viscous solution.

EXAMPLE 2

A polymeric composition was formulated by mixing 30% by weight of the hydrophobic bioabsorbable polymer used in Example 1 with 70% by weight of polyethylene oxide methyl ether having a molecular weight of 350 daltons. The mixture was heated to 80° C. and stirred for 5 days until dissolution was complete.

EXAMPLE 3

A polymeric composition was formulated by mixing 40% by weight of the hydrophobic bioabsorbable polymer used in Example 1 with 60% by weight of polyethylene oxide methyl ether having a molecular weight of 350 daltons. The mixture was heated to 80° C. and stirred for 5 days until dissolution was complete.

EXAMPLE 4

The polymeric composition formulated in Example 1 was placed in the reservoir of an air brush and sprayed onto water. An opaque white film formed on the surface of the water. After repeated spraying the film could be removed with tweezers.

EXAMPLE 5

The polymeric composition formulated in Example 1 was placed in the reservoir of an air brush and was sprayed in vivo onto porcine tissue. The polymeric composition sprayed evenly onto the tissue. Upon contact with the tissue the polymeric composition underwent macroscopic phase separation and formed a transparent/translucent film. The film adhered to the tissue and could be pulled up as a solid sheet. After 4 hours, the film became translucent/opaque and had a wheat color. The film remained integrated and could be pulled off as a solid sheet. No acute irritation of tissue was noted.

EXAMPLE 6

20 grams of the hydrophobic bioabsorbable polymer made according to Example 1 was added in small quantities while stirring at 80° C. to a polymeric composition having 41.5 grams of polyethylene glycol methyl ether (number average molecular weight of 350 having a viscosity of 4.1 centistokes at 210° F.) and 27.5 grams of the hydrophobic bioabsorbable polymer made according to Example 1. The resulting polymeric composition contained 53% by weight of the hydrophobic bioabsorbable polymer. Injection of this polymeric composition into an aqueous medium resulted in the formation of a cheese-like porous mass.

EXAMPLE 7

12.73 grams of the hydrophobic bioabsorbable polymer made according to Example 1 was added in small quantities to 25.7 grams of a polymeric composition made according to Example 6 and heated at 80° C. until completely dissolved. The resulting polymeric composition contained 11.82 grams of polyethylene glycol methyl ether (number average molecular weight of 350 having a viscosity of 4.1 centistokes at 210° F.) and 26.60 grams of the hydrophobic bioabsorbable polymer made according to Example 1. The resulting polymeric composition contained 69.0% weight percent of the hydrophobic bioabsorbable polymer. Injection of this polymeric composition into an aqueous medium resulted in formation of a cheese-like porous mass.

It will be understood that various modifications may be made to the embodiments disclosed herein. Therefore, the above description should not be construed as limiting, but merely as exemplifications within the scope and spirit of the claims appended hereto.

What is claimed is:

1. A liquid polymeric composition comprising a hydrophobic bioabsorbable polymer admixed with a hydrophilic liquid polymer wherein the polymeric composition undergoes macroscopic phase separation on contact with an aqueous environment.

2. The polymeric composition of claim 1 wherein the hydrophilic liquid polymer is poly(alkylene oxide) alkyl ether.

3. The polymeric composition of claim 1 wherein the hydrophilic liquid polymer is poly(alkylene oxide).

4. The polymeric composition of claim 1 wherein the hydrophobic bioabsorbable polymer is selected from the group consisting of polyhydroxyacids, polylactones, polycarbonates, polyanhydrides, polyesteramides, polyorthoesters, polyetheresters, polysaccharides, poly(alkylene oxide) containing polymers, and copolymers, terpolymers and blends thereof.

5. The polymeric composition of claim 2 wherein the poly(alkylene oxide) alkyl ether is poly(ethylene oxide) methyl ether.

6. The polymeric composition of claim 1 wherein the hydrophobic bioabsorbable polymer is derived from a member selected from the group consisting of lactide, glycolide, caprolactone, trimethylene carbonate, copolymers, terpolymers and blends thereof.

7. The polymeric composition of claim 6 wherein the hydrophobic bioabsorbable polymer is a copolymer of about 50% by weight of a block of about 20% by weight glycolide and about 80% by weight trimethylene carbonate, and about 50% of a block of about 20% by weight glycolide and about 80% by weight lactide.

8. The polymeric composition of claim 7 wherein the hydrophilic liquid polymer is poly(ethylene oxide) methyl ether.

9. The polymeric composition of claim 1 wherein the hydrophilic liquid polymer is selected from the group consisting of oxalates of polyoxyalkylene and copolymers of alkylene oxides.

10. The polymeric composition of claim 9 wherein the oxalates of polyoxyalkylene is polyoxyethylene oxalate.

11. The polymeric composition of claim 1 wherein the hydrophilic liquid polymer is polyethylene oxide having a molecular weight less than about 1000 daltons.

12. The polymeric composition according of claim 9 wherein the hydrophilic liquid polymer is a copolymer of polyethylene oxide and polypropylene oxide.

13. A method of forming a bioabsorbable implant comprising:
   providing a hydrophobic bioabsorbable polymer;
   providing a hydrophilic liquid polymer;
   mixing the hydrophobic bioabsorbable polymer with the hydrophilic liquid polymer to form a liquid mixture;
   contacting the mixture with an aqueous liquid to cause macroscopic phase separation of the bioabsorbable polymer; and
   depositing the bioabsorbable implant over a suitable surface.

14. A method of forming a bioabsorbable implant according to claim 13 wherein the suitable surface is body tissue.

15. A method of forming a bioabsorbable implant according to claim 13 wherein the liquid mixture is contacted with an aqueous liquid by spraying the mixture onto the aqueous liquid.

16. A method of forming a bioabsorbable implant according to claim 15 wherein the aqueous liquid is body fluid.

17. A method of forming a bioabsorbable implant according to claim 14 wherein the suitable surface is contained within the mouth of a living creature.

18. A method of forming a bioabsorbable implant according to claim 13 wherein the bioabsorbable implant is a post-surgical adhesion barrier.

19. A method of forming a bioabsorbable implant according to claim 13 wherein the suitable surface is a suture line of a wound.

20. A method of forming a bioabsorbable implant according to claim 13 wherein the implant deposited over the suitable surface is an irregular mass, a regular mass, film or a foam.

21. A method of forming a bioabsorbable implant according to claim 20 wherein the implant is microporous.

* * * * *